United States Patent
Sala et al.

(10) Patent No.: US 10,166,382 B2
(45) Date of Patent: Jan. 1, 2019

(54) DEVICE FOR BREAKING CANNULAS OF HEMATIC SACS OR SIMILAR, AND CORRESPONDING METHOD

(71) Applicant: DELCON SRL, Milan (IT)

(72) Inventors: Norberto Sala, Arcore (IT); Massimo Racanelli, Paolo (IT)

(73) Assignee: DELCON SRL, Milan (IT)

(*) Notice: Subject to any disclaimer, the term of this patent is extended or adjusted under 35 U.S.C. 154(b) by 639 days.

(21) Appl. No.: 14/647,819

(22) PCT Filed: Nov. 28, 2013

(86) PCT No.: PCT/IB2013/002664
§ 371 (c)(1),
(2) Date: May 27, 2015

(87) PCT Pub. No.: WO2014/083412
PCT Pub. Date: Jun. 5, 2014

(65) Prior Publication Data
US 2015/0306371 A1    Oct. 29, 2015

(30) Foreign Application Priority Data
Nov. 28, 2012 (IT) ............... MI2012A2028

(51) Int. Cl.
*A61M 39/22* (2006.01)
*A61M 1/02* (2006.01)

(52) U.S. Cl.
CPC ........ *A61M 39/221* (2013.01); *A61M 1/0209* (2013.01); *A61M 2039/222* (2013.01)

(58) Field of Classification Search
CPC . B65B 69/00; B65B 69/0008; B65B 69/0016; A61M 39/146; A61M 39/28; A61M 1/0209; A61M 1/0236; A61B 17/122; A61B 17/1225

USPC ................ 53/492, 381.1; 604/403; 383/200; 225/1, 103
See application file for complete search history.

(56) References Cited

U.S. PATENT DOCUMENTS

| | | | | |
|---|---|---|---|---|
| 6,132,413 A | * | 10/2000 | Mathias | A61M 39/221 604/403 |
| 6,692,479 B2 | * | 2/2004 | Kraus | A61B 5/412 604/32 |
| 2003/0138349 A1 | * | 7/2003 | Robinson | A61M 1/02 422/44 |
| 2010/0132512 A1 | * | 6/2010 | Bucciaglia | A61M 39/221 81/3.2 |
| 2010/0186349 A1 | * | 7/2010 | Zanini | B65B 7/2835 53/317 |
| 2013/0256576 A1 | * | 10/2013 | Deverre | A61M 39/221 251/215 |

FOREIGN PATENT DOCUMENTS

WO    WO-2012/080664 A2    6/2012

OTHER PUBLICATIONS

Search Report for PCT/IB2013/002664, dated Mar. 3, 2014.

* cited by examiner

*Primary Examiner* — Andrew M Tecco
*Assistant Examiner* — Nicholas Igbokwe
(74) *Attorney, Agent, or Firm* — Marshall, Gerstein & Borun LLP (57) ABSTRACT

A device for breaking cannulas of sacs comprises a breaking head, and replaceable means for positioning and breaking a cannula which can be driven by the breaking head.

14 Claims, 8 Drawing Sheets fig. 1 fig. 2a fig. 2b fig. 4 fig. 5 fig. 7 fig. 6 fig. 11 fig. 11a fig. 11b fig. 11c fig. 12 fig. 13a fig. 13 fig. 13b fig. 13e fig. 13c fig. 13d fig. 13d fig. 13f

DEVICE FOR BREAKING CANNULAS OF HEMATIC SACS OR SIMILAR, AND CORRESPONDING METHOD

FIELD OF THE INVENTION

The present invention concerns a device and corresponding method, for breaking cannulas, or breakable valves, present in hematic sacs, or in elements similar or comparable to hematic sacs. A device for breaking cannulas on which the preamble of the independent claims is based is described in WO2012/080664A2.

BACKGROUND OF THE INVENTION

It is known that in specialized centers, hospitals or production centers of blood components, a large number of hematic sacs are processed daily to satisfy the needs of transfusion and of the pharmaceutical industry of blood derivatives. It is also known that the sacs that contain or will contain hematic material are of different shapes and characteristics depending on the producer.

Each of these sacs has one or more cannulas, or breakable valves, which, at determinate moments, must be opened during the working process.

It is known that breaking these cannulas, or breakable valves, of the sacs, an operation carried out many times if not hundreds, during the day, causes tiredness in the staff involved, and leads to the formation of skin thickening on the fingers used, and sometimes even causes more serious situations.

A method is also known for breaking cannulas, or breakable valves, hereafter called only cannulas, which is partly automatic, on the basis of which the upper part of a cannula is subjected to repeated bending, toward the right and/or toward the left, using the elements of automated equipment, or breaking head, while the part physically connected to the sac is held stationary.

This method is by itself satisfactory, but it is not such as to solve all the problems which there are in a room where the hematic sacs are processed. Indeed, as we said above, sacs of different producers can be worked in this process, so that it is not possible that a single breaking head can satisfy all the different needs which arise, as the type and size of the sac or cannula vary.

To overcome all these disadvantages, the Applicant set himself the purpose of making a device suitable to embody an automatic method for breaking cannulas of hematic sacs even as the type and size thereof vary.

Moreover, the Applicant set himself the purpose of making said device with suitable stratagems so that substantially all the cannulas of the various types of sacs in existence can be broken.

Furthermore, Applicant set himself the purpose of making a machine which can easily be adapted to the requirements of new sacs.

Another purpose is to be able to adapt the machine in a very short time when a new sac arrives, also providing the producer or user of said sac the means to prevent laboratories encountering difficulties when new sacs or cannulas arrive.

These and other purposes and the connected advantages will be evident hereafter in the description.

SUMMARY OF THE INVENTION

The present invention is set forth and characterized in the independent claims, while the dependent claims describe other characteristics of the invention or variants to the main inventive idea.

As we said, the present invention concerns a device usable in association with a machine to receive and treat hematic sacs, for example a machine for the extraction of hematic fractions.

The device of the present invention comprises a breaking head and replaceable means for positioning and breaking a cannula, drivable by the breaking head.

The device of the present invention is suitable for breaking the cannulas of hematic sacs, in which the breaking head is configured to achieve an alternate backward and forward movement to progressively cause the breakage.

According to some forms of embodiment, the backward and forward action, which can be semi-rotating or linear, and which breaks the cannula, is obtained using a drive member which activates a connection element, supplying this with a programmed and programmable work cycle.

According to a first solution, the drive member is substantially in axis with the connection element.

According to a variant, in order to reduce stresses, the drive member is transverse, in particular orthogonal, to the axis of the connection element and connected to it by means of conical toothed wheels for example.

According to the present invention, there are replaceable means for positioning and breaking a cannula drivable by the breaking head, for example provided at the front of the machine and in cooperation with an operating front part of the connection element.

The replaceable means for positioning and breaking a cannula have rapid connection means both to the connection element and to the front part of the operating machine.

The replaceable positioning and breaking means also have position correction means with respect to the connection element.

The replaceable positioning and breaking means, in cooperation with the rapid connection means to the connection element, have two or more mobile pegs, which extend frontally both with respect to the support means and to other pegs, fixed, which cooperate in keeping a part of the cannula stationary.

The mobile pegs are suitable to move forward and backward along a breaking path, for example a semi-circumference, or similar arched or curvilinear segment, or a rectilinear segment, being activated in such movement by the connection element.

It is therefore possible to predispose all the replaceable means needed for all the sacs on the market, or for new sacs too, of different type and size: it is only necessary to correctly position the pegs that move forwards and backwards, and the fixed pegs on new replaceable means.

According to a variant, the pegs which move forwards and backwards, instead of moving along a semi-circumference, move linearly.

In variant forms of embodiment, sac support means can also be present frontally or laterally to the machine.

The sac support means, according to a variant, are replaceable by providing rapid connection means and advantageously have centering means.

The sac support means can be fixed or adjustable and, according to a variant, can be associated to the replaceable positioning and breaking means.

BRIEF DESCRIPTION OF THE DRAWINGS

These and other characteristics of the present invention will become apparent from the following description of some forms of embodiment, given as a non-restrictive example with reference to the attached drawings wherein:

FIG. 1 is a schematic view of a quadruple sac in which the present invention is applied;

FIG. 2a is an exploded view of a first form of embodiment of the device according to the invention;

FIG. 2b is a view of part of the first form of embodiment in FIG. 2a;

FIG. 3b is an exploded view of part of FIG. 3a;

To facilitate comprehension, the same reference numbers have been used, where possible, to identify identical common elements in the drawings.

DETAILED DESCRIPTION OF SOME FORMS OF EMBODIMENT

Forms of embodiment of the present invention concern a device 10 for breaking cannulas or breakable valves 12 of sacs 14, hematic sacs for example, usable in association with a machine for the extraction of hematic fractions.

A cannula or breakable valve 12, as intended in the forms of embodiment described here, is a connection and fluidic interception member mounted on a sac 14 of the type in question and which has a portion or line of predefined breakage, through which the connection and fluidic interception member can be put in a condition which allows the passage of a fluid through it.

Figures 1, 2A, 2B:
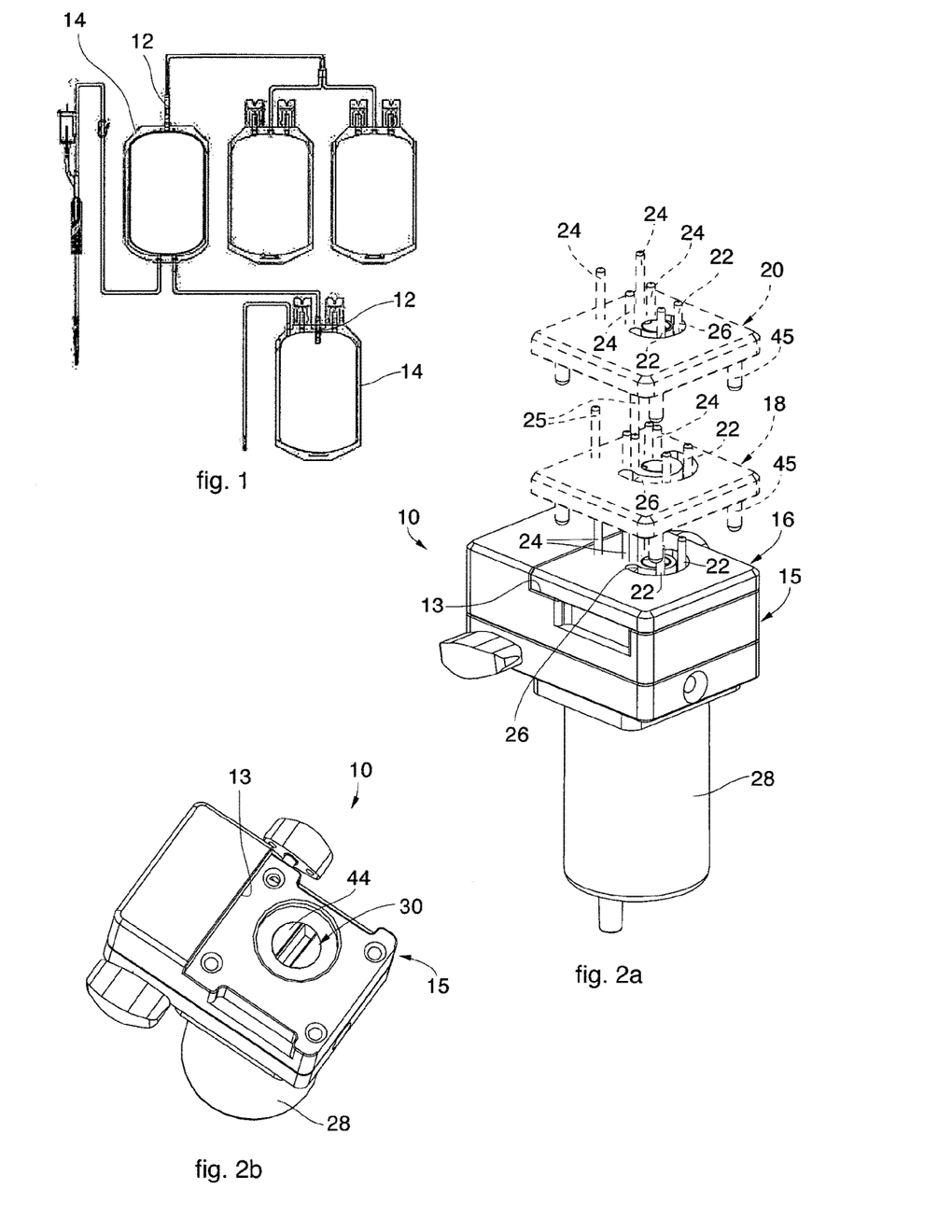

In FIG. 1 a system of multiple sacs 14 is shown to which the present invention can be applied. A system of multiple sacs 14 can be used for example in a machine 60 for extracting hematic fractions as indicated above, shown for example in FIGS. 6 and 8, and configured to automatically prepare sacs 14 containing the fractions from whole blood, used for example for transfusions: i) concentrates of red corpuscles, ii) concentrates of platelets, iii) plasma, iv) buffy-coats, the latter being an intermediate fraction formed from a mixture of plasma, concentrates of red corpuscles, concentrates of white corpuscles and platelets, which are created after the centrifugation of the whole blood. The machine 60 generally obtains said fractioning of the whole blood by means of a controlled sedimentation for fractions, carried out in specially provided centrifuges. The extraction machine 60, by means of the controlled movement of one or two presses used to squeeze the centrifuged sacs, a series of clamps with heads welding the tubes, a plurality of scales, three or more for example, and optical sensors, is able to extract and automatically transfer the hematic fractions from one main sac to a multiplicity of satellite sacs 14, equipped with said cannulas or breakable valves 12.

FIGS. 2a and 2b are used to describe a plurality of forms of embodiment of a device 10 for breaking cannulas 12, which can be combined with other forms of embodiment described here. The device 10 includes a breaking head 15 drivable in a desired manner.

Moreover, the device 10 includes a plurality of replaceable members or means 16, 18, 20 for positioning and breaking cannulas 12.

In forms of embodiment described with reference to FIG. 2a, each of the replaceable positioning and breaking members 16, 18, 20 can be configured as a plate.

Each of the replaceable positioning and breaking members 16, 18, 20 can be mounted, on each occasion, on the breaking head 15, in order to adapt to the different types of existing sacs 14 and cannulas 12. For example, the breaking head 15 can have a lowered seating 13 (FIG. 2b) in which to place on each occasion one of said replaceable positioning and breaking members 16, 18, 20, which is advantageously positionable flush with the external surface of the breaking head 15 as can be seen in FIG. 2a.

The breaking head 15 is configured to define a forward and backward movement of the replaceable positioning and breaking member 16, 18, 20 which is generally connected to it. The alternate forward and backward movement is provided to selectively bend a cannula 12 from one side to the other, in order to cause the breakage and thus the opening thereof.

Each replaceable positioning and breaking member 16, 18, 20 can include two or more mobile breaking pegs 22, distanced from each other in a desired manner in order to define a passage or channel 23 (FIG. 3c, 3d, 3e), advantageously with play, in which a part of at least one cannula 12 to be broken is positioned. The mobile breaking pegs 22 can be rotated angularly. The mobile breaking pegs 22 are driven in rotation by the breaking head 15, or, in other variants, the mobile breaking pegs 22 can be moved linearly.

In some forms of embodiment, the mobile breaking pegs 22 can be aligned with each other along a transverse direction, orthogonal for example, to the direction of insertion of the cannula 12 to be broken between them.

Moreover, each replaceable positioning and breaking member 16, 18, 20 can have a through eyelet 26, shaped semi-circular for example or in any case comparable to an arched segment, or in other variants shaped linear, inside which the mobile breaking pegs 22 can slide along a desired forward and backward path that causes a flexing and bending in a clockwise and anti-clockwise direction, or from one side to the other, of part of the cannula 12 so that it breaks.

Each replaceable positioning and breaking member 16, 18, 20 can include fixed contrast pegs 24, which cooperate in clamping a part of the cannula 12, in particular during the breaking action. For example, the mobile breaking pegs 22 extend frontally with respect to the fixed contrast pegs 24. The fixed contrast pegs 24 can be configured as one or more couples and distanced from each other so as to define an insertion passage or channel 27, in this case too with a desired play, in order to receive the part of the cannula 12 to be contrasted.

In some forms of embodiment, the fixed contrast pegs 24 of a specific pair can be aligned with each other along a transverse direction, for example orthogonal, to the direction of insertion of the cannula 12 to be contrasted between them.

In some forms of embodiment, a motor 28 is provided which activates and moves in rotation a connection element 30 of the breaking head 15, supplying the latter with an alternate motion in accordance with a work cycle. The motor 28 can be connected in axis with the connection element 30, as shown for example in FIGS. 2a and 2b.

Figure 3A:
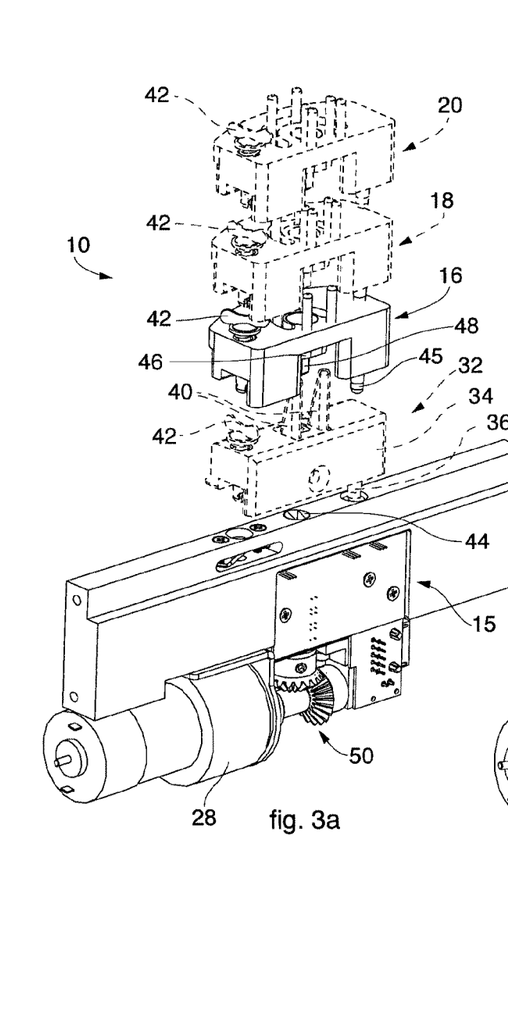
FIG. 3a is an exploded view of a second form of embodiment of the device according to the invention.
Figure 3B:
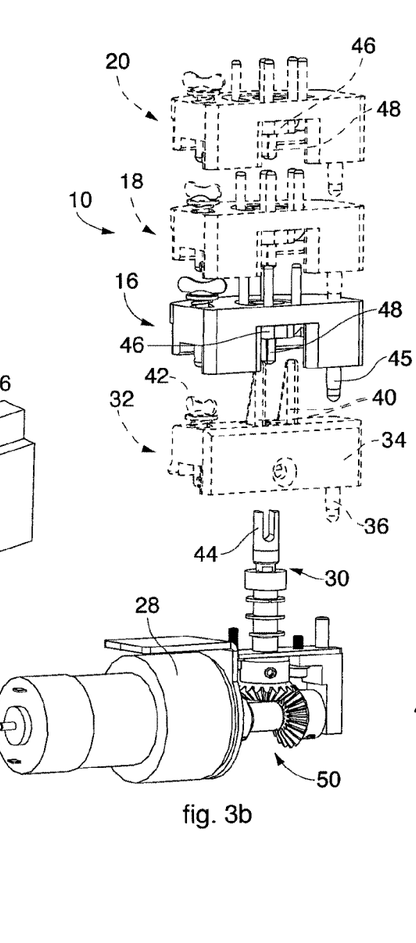

FIGS. 3a and 3b are used to describe a plurality of forms of embodiment of a device 10 for breaking cannulas 12, which can be combined with other forms of embodiment described here, in which the motor 28 is transverse, for example orthogonal, to the axis of the connection element 30 and connected to it, for example by means of conical toothed wheels 50.

In some forms of embodiment, the connection element 30 can be kinematically connected to the replaceable positioning and breaking members 16, 18, 20 which on each occasion can be mounted on the breaking head 15. In some forms of embodiment, the connection element 30 can include a fork-type connection end 44 which acts as a front operating part of the connection element 30.

For example, each of the replaceable positioning and breaking members 16, 18, 20 can include a rotary carousel 46, formed for example by a disc or a rotating platform in general, on which the mobile breaking pegs 22 are disposed.

To adapt to the different positioning geometries required by the various types of cannulas 12 to be broken, the mobile breaking pegs 22 themselves can be positionable and replaceable with respect to a rotary carousel 46, or it may be provided that for example the combination formed by the rotary carousel 46 and mobile breaking pegs 22 is replaceable by another rotary carousel 46 having the mobile breaking pegs 22 in a different configuration.

The rotating carousel 46 can have at its lower part a rapid connection portion 48 to be inserted into the fork end 44. In some forms of embodiment, each of the replaceable positioning and breaking members 16, 18, 20 comprises at least one centering peg or other mean 45, which can function as a correct positioning element with respect to the connection element 30.

In some forms of embodiment, sac support means can be provided, such as in this case a support unit 32 (FIGS. 3a, 3b and 3f) for the sac 14 which can include for example a base body 34 from which at least a centering peg or analogous mean 36 projects. The base body 34 can also include for example at least a rapid connection element or mean 42 of the releasable type, usable in this case for connection, for example at the front, to the machine for extracting hematic fractions.

The support unit 32 can have a fork that includes two tines or arms, or analogous means 40 that support the sac 12 which, for example protrude from the base body 34, in this case on the opposite side with respect to the at least one centering peg 36. In some forms of embodiment, the support means 40 are configured to support the sac so that it is possible to intervene manually on the cannula 12 in order to break it. In particular, the support means 40 can be made with two ends with a conical shape, since based on the depth of manual positioning of the cannula 12 it is possible to raise or lower the point of breakage of the cannula 12.

In some forms of embodiment, the support unit 32 is a separate component, and therefore replaceable and positionable as required on the machine 60, with respect to the replaceable positioning and breaking members 16, 18, 20, which can be mounted on the breaking head 15 and can be connected on each occasion to the machine 60.

Figure 3C:
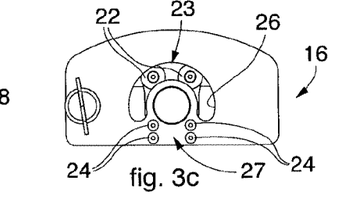
FIGS. 3c-3f are plan views of different interchangeable parts of the present invention.
Figure 3D:
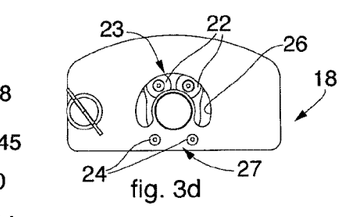
Figure 3E:
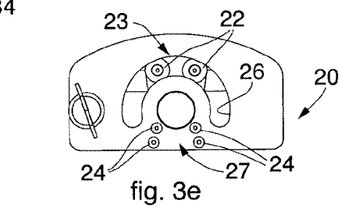
Figure 3F:
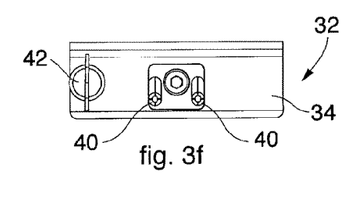

FIGS. 3c-3e are used to describe forms of embodiment of replaceable positioning and breaking members 16, 18, 20, which can be combined with other forms of embodiment described here and which can be selected on each occasion depending on the type of sac 14.

A first replaceable positioning and breaking member 16 is shown in FIG. 3c and can include two pairs of fixed contrast pegs 24 disposed along parallel and opposite directions of alignment, and a pair of mobile breaking pegs 22, distanced from each other by a desired length, with the provision that the directions of alignment are in turn parallel to a direction of insertion of the cannula 12 between the fixed contrast pegs 24 and the mobile breaking pegs 22.

A second replaceable positioning and breaking member 18 is shown in FIG. 3d and can include a single pair of fixed contrast pegs 24 and a pair of mobile breaking pegs 22 which in this variant are closer together than in FIG. 3c.

A third replaceable positioning and breaking member 20 is shown in FIG. 3e and can include two pairs of fixed contrast pegs 24 disposed along directions converging toward the inside, and a pair of mobile breaking pegs 22 which in this variant are distanced as in FIG. 3c.

Figure 4:
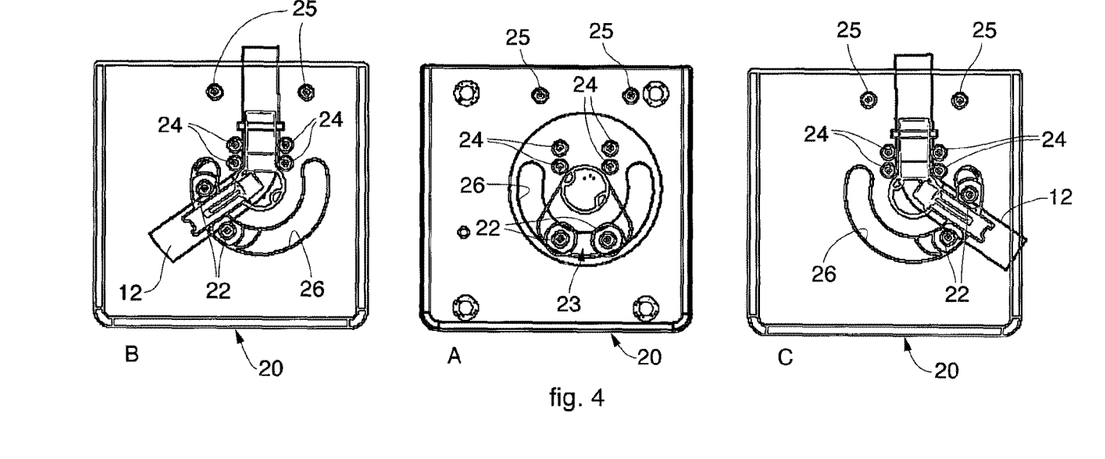
FIG. 4 shows functioning models of the device according to the present invention.

FIG. 4 is used to describe models A, B and C of steps of breaking a cannula by means of one of the replaceable positioning and breaking members 16, 18, 20, for example the third replaceable positioning and breaking member 20. Model A in FIG. 4 shows for example the first replaceable positioning and breaking member 16 in a starting condition for the insertion of the cannula 12 between the mobile breaking pegs 22 and the fixed contrast pegs 24, model B shows how the first replaceable positioning and breaking member 16 is driven to rotate the mobile breaking pegs 22 in a clockwise direction and cause the cannula 12 to bend toward the left, and finally model C shows how the first replaceable positioning and breaking member 16 is driven to rotate the mobile breaking pegs 22 in an anti-clockwise direction and cause the cannula 12 to bend to the right.

Figure 5:
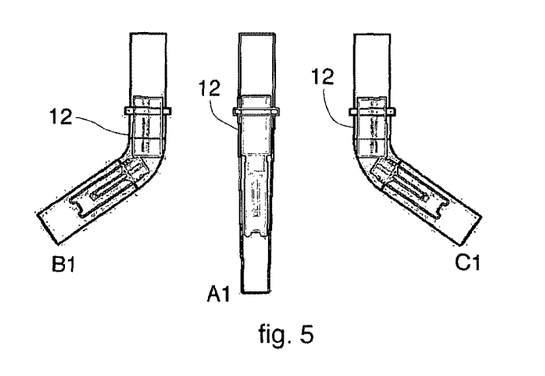
FIG. 5 shows the effects on the cannulas of the movements of the device shown in FIG. 4.

FIG. 5 is used to describe models A1, B1, C1 of a cannula 12 in relation to models A, B, C in FIG. 4. Model A1 shows the cannula 12 ready to be inserted for example into the first replaceable positioning and breaking member 16 of model A in FIG. 4, model B1 shows the cannula 12 bent according to model B in FIG. 4 and model C1 shows the cannula 12 bent according to model C in FIG. 4.

FIGS. 6-10 are used to describe a plurality of forms of embodiment, which can be combined with other forms of embodiment described here, in which a device 10 for breaking cannulas 12 is integrated with a machine 60 for extracting hematic fractions. The machine 60 can include a front bracket 62 for positioning the device 10, which is accessed for example by means of a door 64. The machine 60 can include at least a vertical rod 61 (FIGS. 6 and 8), possibly provided with a support bracket 63, adjustable in height, with the possibility of sliding along said vertical rod 61. The vertical rod 61 can be used to support an auxiliary or additional device of the machine 60, for example a device 10 for breaking cannulas mounted vertical, as will be described hereafter using FIGS. 11-12.

Figure 6:
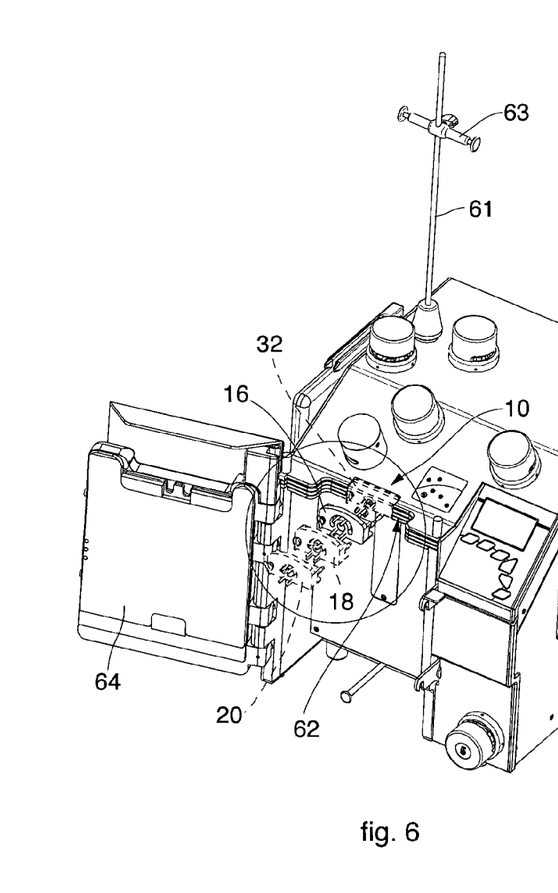
FIG. 6 shows one form of embodiment of the present invention.
Figure 7:
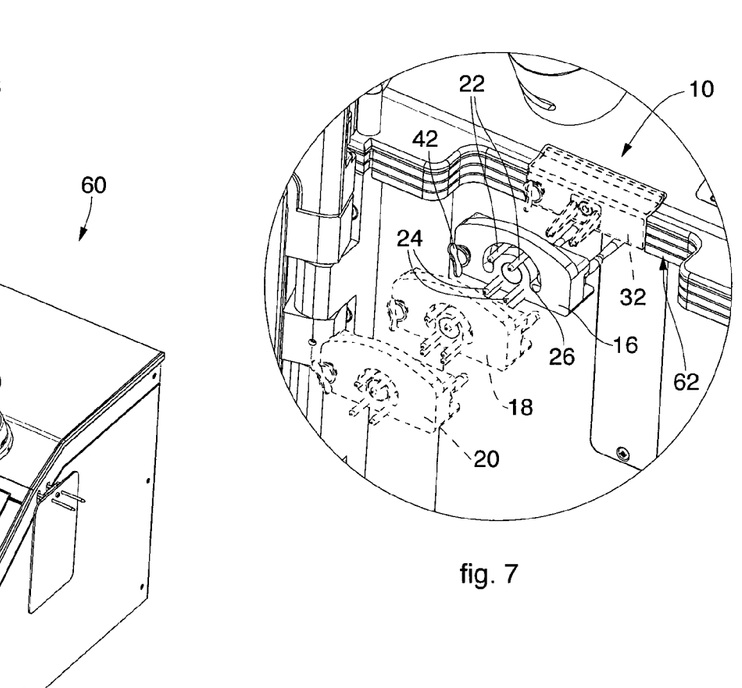
FIG. 7 shows an enlarged detail of FIG. 6.
Figures 8, 9, 10:
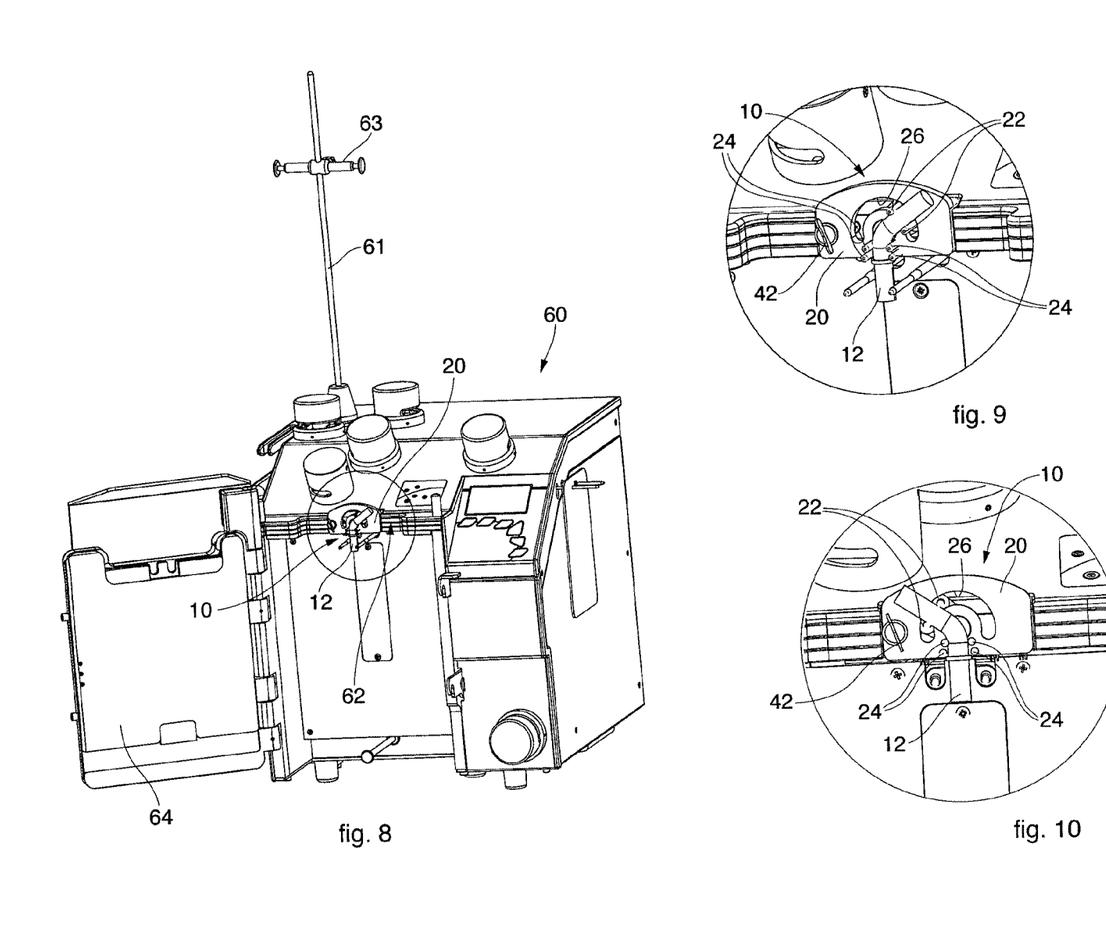
FIG. 8 shows the form of embodiment in FIG. 6 in a condition of use.
FIG. 9 and FIG. 10 show, in two different positions, a detail of the form of embodiment in FIG. 6.

In FIG. 6 the replaceable positioning and breaking members 16, 18, 20 can be seen, which can be adopted depending on the sacs 14. The detail in FIG. 7 is used to describe the positioning of one or the other of the replaceable positioning and breaking members 16, 18, 20 with respect to the support unit 32 attached to the front bracket 62. FIG. 8 is used to describe how a cannula 12 can be bent for breaking by one of the replaceable positioning and breaking members 16, 18, 20, for example the third replaceable positioning and breaking member 20. The detail in FIG. 9 shows the bending of the cannula 12 in a clockwise direction, while the detail in FIG. 10 shows the bending of the cannula 12 in an anti-clockwise direction.

Figure 11:
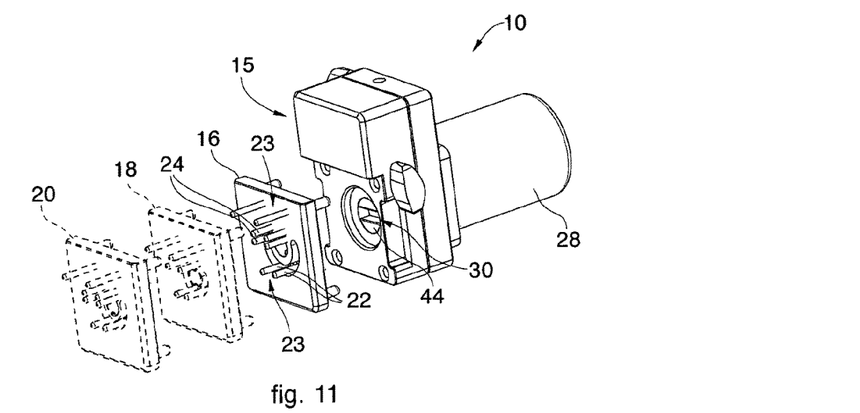
FIG. 11 shows another form of embodiment of the present invention.
Figure 11A:
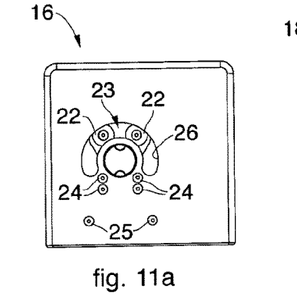
FIGS. 11a, 11b and 11c show plan views from above of variants of a part of FIG. 11.
Figure 11B:
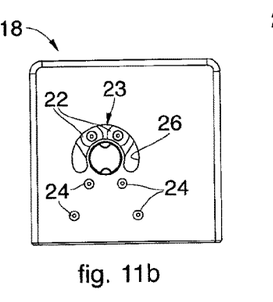
Figure 11C:
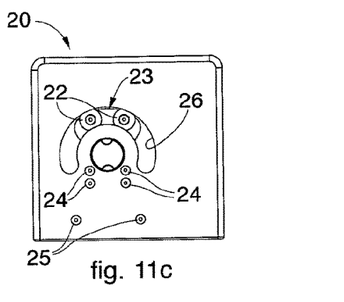
Figure 12:
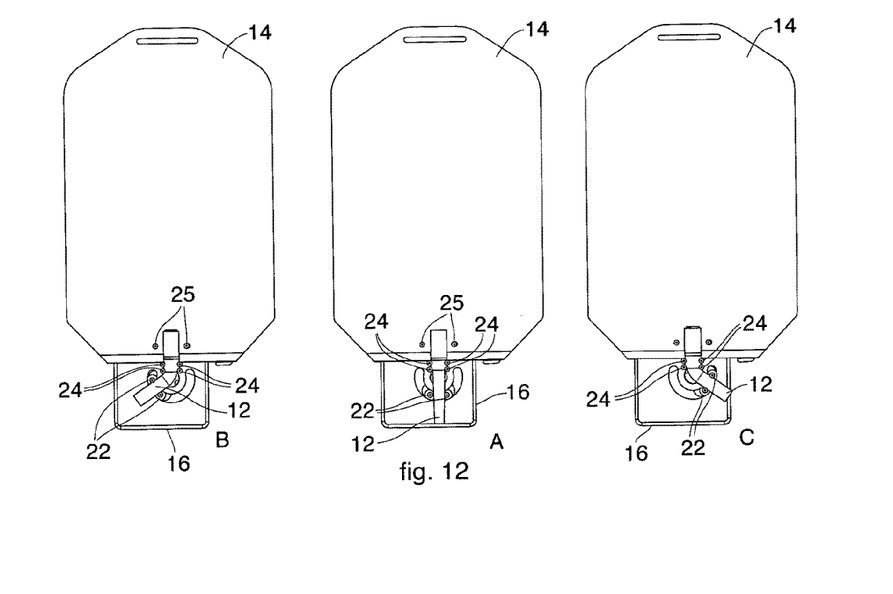
FIG. 12 shows functioning models of the form of embodiment in FIG. 11.

FIGS. 11-12 are used to describe a plurality of forms of embodiment, which can be combined with other forms of embodiment described here, in which a device 10 for breaking cannulas 12 is configured to be mounted on a vertical rod 61 of a machine 60 for extracting hematic fractions as described for example using FIGS. 6 and 8. The device 10 comprises forms of embodiment of the replaceable positioning and breaking members 16, 18, 20, as described for example using FIGS. 2a and 2b, also visible in FIG. 11 and shown plan for example in FIGS. 11a-11c. Each of the replaceable positioning and breaking members 16, 18, 20 of FIGS. 11a-11c, comprises mobile breaking pegs 22, between which a cannula 12 to be broken can be positioned. The mobile breaking pegs 22 can be rotated, in order to break the cannulas 12. The mobile breaking pegs 22 can be configured in the same way as described with reference to FIGS. 3c-3e, with the provision that:

a first replaceable positioning and breaking member 16 in FIG. 11a can include two pairs of fixed contrast pegs 24 disposed along parallel directions, similar to FIG. 3c, and also a third pair of fixed pegs for anchoring the sac 25 disposed externally with respect to the two pairs of fixed contrast pegs 24. In the third pair of fixed pegs for anchoring the sac 25, the latter are distanced from each other more than the fixed contrast pegs 24 of the two internal pairs, so as to define an alignment geometry in directions converging toward the inside between an outermost pair of fixed contrast pegs 24 and the third pair of fixed pegs for anchoring the sac 25;

a second replaceable positioning and breaking member 18 in FIG. 11b is identical to the first replaceable positioning and breaking member 16 in FIG. 11a, wherein however the two pairs of fixed contrast pegs 24 are configured with the fixed contrast pegs 24 disposed on one side and the other along directions converging toward the inside, similar to FIG. 3d although at a greater distance from each other compared with FIG. 3d;

a third replaceable positioning and breaking member 20 in FIG. 11c is identical to the first replaceable positioning and breaking member 16 in FIG. 11a, wherein however the size of the through eyelet 26, for example in terms of width and/or radius of the correlated circumference, is different, in this case bigger.

FIG. 12 is used to describe models A, B and C of steps of breaking a cannula by means of one of the replaceable positioning and breaking members 16, 18, 20, for example the third replaceable positioning and breaking member 20, as described using for example FIG. 2a, 2b or 11.

Figure 13:
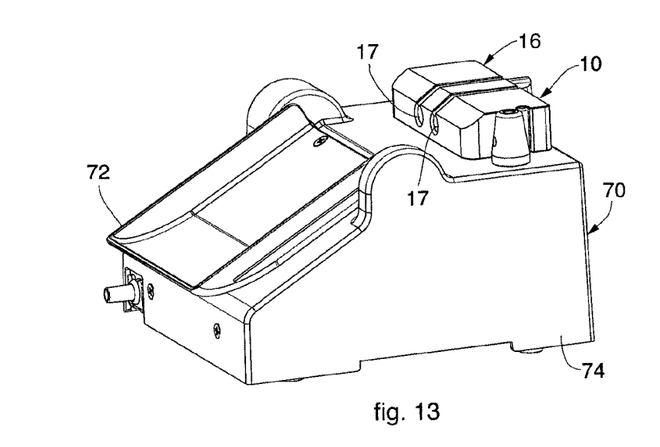
FIG. 13 shows yet another form of embodiment of the present invention.
Figure 13A:
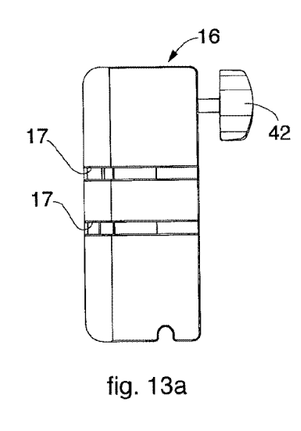
FIGS. 13a, 13b, 13c, 13d, 13e, 13f show plan views from above and from the side of variants of a part of FIG. 13.
Figure 13B:
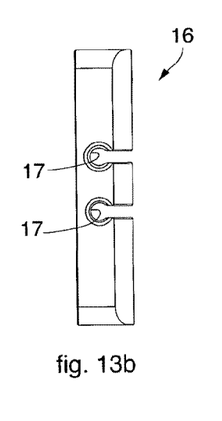
Figure 13C:
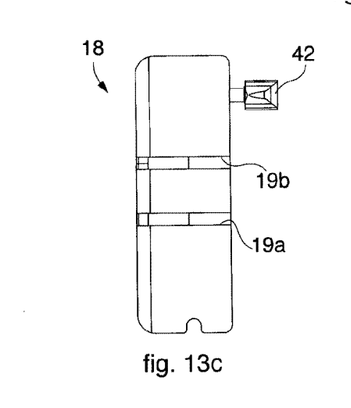
Figure 13D:
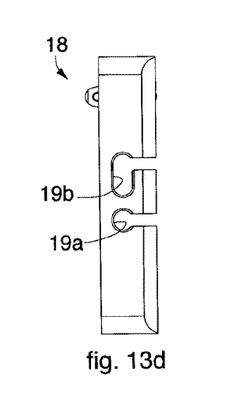
Figure 13E:
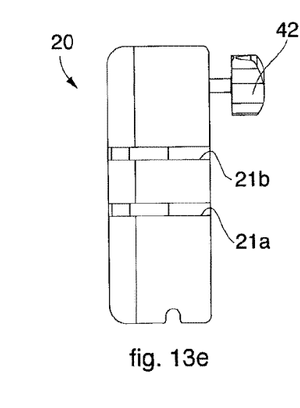
Figure 13F:
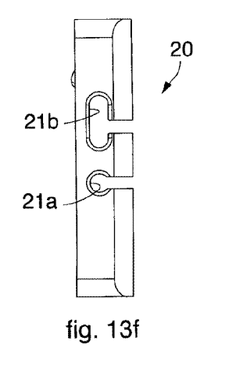
Figure 14:
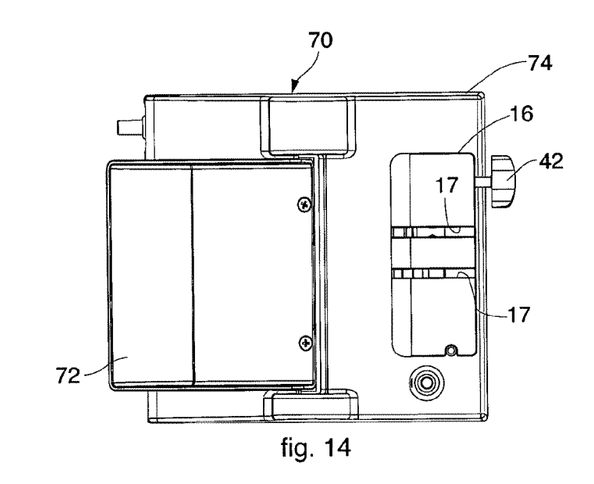
FIG. 14 shows the form of embodiment in FIG. 13 configured to cooperate with an auxiliary device.
Figure 14A:
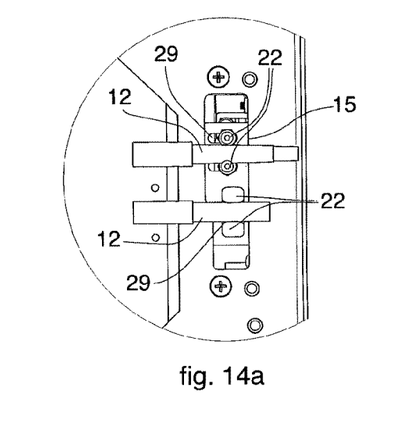
FIGS. 14a, 14b, 14c show functioning models of the form of embodiment in FIG. 13 configured as shown in FIG. 14.
Figure 14B:
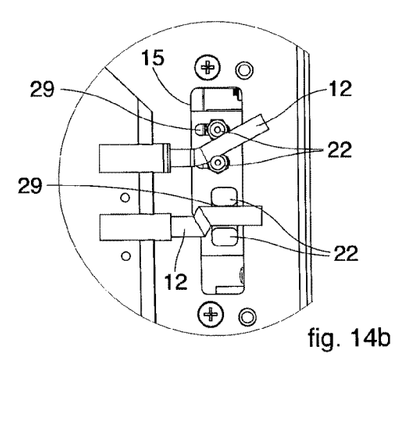
Figure 14C:
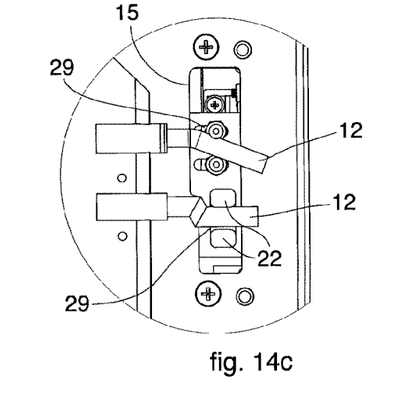

FIGS. 13-14c are used to describe a plurality of forms of embodiment, which can be combined with other forms of embodiment described here, in which a device 10 for breaking cannulas 12 is mounted for example on a device 70 for mixing the content of a sac 14, for example to mix red corpuscles with a nutrient solution, for example used with a machine 60 for extracting hematic fractions. The mixing device 70 can include an oscillating tray 72 mounted on a base body 74, functioning as a sac support and also oscillation mean. The device 10 can for example be mounted above the base body 74. The device 10 comprises the replaceable positioning and breaking members 16, 18, 20, shown for example in FIGS. 13a-13f. Each of the replaceable positioning and breaking members 16, 18, 20 comprises fixed contrast pegs 24 and is associated with mobile breaking pegs 22. The latter can be provided, as shown in FIGS. 14a-14c, on the breaking head 15 below, mounted on the base body 74, and therefore not disposed on the replaceable positioning and breaking members 16, 18, 20. Or in other variants, not shown here, the mobile breaking pegs 22 can be provided on the replaceable positioning and breaking members 16, 18, 20. Between the mobile breaking pegs 22 a cannula 12 to be broken can be positioned. For example, at least a pair of mobile breaking pegs 22 can be provided, disposed adjacent, for example mounted on a slider 29 able to slide linearly (FIGS. 14a-14c), at a desired distance from each other, which can be selected depending on the type of cannula 12 to be broken.

In other forms of embodiment, two pairs of mobile breaking pegs 22 can be provided, aligned along a common direction of movement, or aligned along different directions of movement and parallel to each other, to break two cannulas 12 as for example provided in FIGS. 14a-14c, with the provision that the common direction of movement or the directions of movement are transverse to a direction of insertion of the cannula 12 to be broken between the mobile breaking pegs 22.

In this case too, to adapt to the different positioning geometries required by the various types of cannulas 12 to be broken, the mobile breaking pegs 22 can be positioned and replaced with respect to the sliding slider 29, or it can be provided that the combination formed by the sliding slider 29 and mobile breaking pegs 22 be replaced by another sliding slider 29 having the mobile breaking pegs 22 in a different configuration.

The mobile breaking pegs 22 can be moved linearly, using the breaking head 15 which can act on the sliding slider 29, for example along suitable linear through eyelets, not visible in the drawings. This linear movement can be alternated along a direction of breaking, causing the one or more cannulas 12 to bend one way and the other and then to break.

FIGS. 13a-13f are used to describe forms of embodiment of replaceable positioning and breaking members 16, 18, 20 which can be used for example in the device 10 mounted on the mixing device 70 and which can be combined with other forms of embodiment described here.

FIGS. 13a and 13b show, plan and laterally, a first replaceable positioning and breaking member 16 which includes two longitudinal housings 17, for example adjacent and parallel, to insert the cannulas 12 for breaking. Each housing 17 is conformed to house only specific cannulas 12. In this form of embodiment, the housings 17 are all identical and have an essentially circular cross section with suitable diameters for the different cannulas 12, which can also be different in length, within the framework of the individual housing 17, as visible in the attached drawings. For example, the housings 17 can be provided longitudinally with a first segment having a bigger diameter and a second segment that narrows with a smaller diameter.

FIGS. 13c and 13d show, plan and laterally, a second replaceable positioning and breaking member 18 which includes two longitudinal housings 19a, 19b, for example adjacent and parallel, which, in this form of embodiment, can be different from each other, for example to receive different types of cannulas 12 in terms of width or length, for example one housing 19a with an essentially circular section and one housing 19b with a cross section that is partly curved and partly linear, wider on an internal side toward the housing 19a. This different configuration of the housings 17 can facilitate the simultaneous breaking of cannulas 12 having different sizes or conformation.

FIGS. 13e and 13f show, plan and laterally, a third replaceable positioning and breaking member 20 which includes two housings 21a, 21b, which, in this form of embodiment too, can be different from each other, in this case too for example to receive different types of cannulas 12 in terms of width or length, for example one housing 21a with an essentially circular section and one housing 21b with a cross section that is partly curved and partly linear, wider on an external side with respect to the housing 21a. This different configuration of the housings 17 can also facilitate the simultaneous breaking of cannulas 12 having different sizes or conformation.

FIGS. 14a-14c are used to describe models of steps of breaking a cannula 12 using one of the replaceable positioning and breaking members 16, 18, 20 of FIGS. 13a-13f, for example the first replaceable positioning and breaking member 16, in which the mobile breaking pegs 22 are driven linearly, along a transverse direction, for example orthogonal, to the direction of insertion of the cannulas 12 between the mobile breaking pegs 22, on one side and the other in order to bend the cannulas 12. In FIG. 14a one can see how it is possible to operate on two different cannulas 12 simultaneously.

It is clear that modifications and/or additions of parts and/or steps may be made to the device 10 for breaking cannulas of hematic sacs or suchlike, and the corresponding method, as described heretofore, without departing from the field and scope of the present invention.

The invention claimed is:

1. Device for breaking cannulas of sacs comprising a breaking head, and replaceable means for positioning and breaking a cannula which can be driven by the breaking head, wherein said replaceable means are associated to a plurality of mobile breaking pegs, wherein said breaking head is configured to make an alternate backward and forward movement, along an arched or curvilinear segment, or along a linear segment, of said mobile breaking pegs, and wherein the replaceable means comprise at least two fixed contrast pegs, wherein the replaceable means includes a plurality of replaceable members, wherein at least the fixed contrast pegs and/or the mobile breaking pegs associated to at least one of said replaceable members are configured in a different way with respect to at least one other of said replaceable members,
wherein each of the replaceable means includes a rotary carousel on which the mobile breaking pegs are disposed,
wherein the mobile breaking pegs are positionable and replaceable with respect to the rotary carousel and/or are positionable and replaceable with respect to the combination formed by the rotary carousel and the mobile breaking pegs,
wherein the rotary carousel has a lower part having a rapid connection portion configured to be inserted in a fork end of a connection element of a motor for kinematically connecting the motor to the replaceable means.

2. Device as in claim 1, wherein said replaceable members comprise at least a through eyelet, configured arched or curvilinear, or linear, and wherein at least one of said mobile breaking pegs is positioned inside a the through eyelet.

3. Device as in claim 1, wherein said drive motor is disposed along an axis of said connection element or transverse to said connection element.

4. Device as in claim 1, wherein said replaceable members comprise a rapid connector.

5. Device as in claim 1, wherein the device further comprises a sac support.

6. Device as in claim 5, wherein said sac support includes a rapid connector.

7. Device as in claim 1, wherein at least one of said replaceable members comprises at least two pairs of fixed contrast pegs disposed along parallel and opposite directions, and a pair of mobile breaking pegs.

8. Device as in claim 1, wherein at least one of said replaceable members comprises at least two pairs of fixed contrast pegs disposed along directions converging toward the inside and opposite with respect to each other, and a pair of mobile breaking pegs.

9. Device as in claim 1, wherein at least one of said replaceable members comprises one or more longitudinal housings to receive the cannula, each longitudinal housing being associated to a pair of said mobile breaking pegs, wherein the longitudinal housings can be identical to each other and have an essentially circular section, or the longitudinal housings can be different from each other and having different diameters, and wherein one of the longitudinal housings has a circular section and another one of the longitudinal housings has a partly curved and a partly linear section.

10. Device as in claim 1, wherein the device is operatively coupled in a machine for extracting hematic fractions.

11. Method for breaking cannulas of sacs, comprising:
using the device of claim 1; and
selecting the replaceable means for positioning and breaking cannulas depending on a type and/or a size of said cannulas.

12. Device as in claim 4, and further including correct positioning means.

13. Device as in claim 6, and further including centering means.

14. Device as in claim 1, wherein at least one of said replaceable members for positioning and breaking a cannula comprises one or more longitudinal housings, wherein one of the longitudinal housings is widened on an internal side, and wherein one of the longitudinal housings has an essentially circular section and another one of the longitudinal housings has a partly curved and a partly linear section and is widened on one external side.

* * * * *